United States Patent [19]
Ito et al.

[11] Patent Number: 6,008,246
[45] Date of Patent: *Dec. 28, 1999

[54] EXTERNAL PREPARATION FOR SKIN CONTAINING A LOW-MOLECULAR-WEIGHT BETAINE

[75] Inventors: Kenzo Ito; Haruhiko Inoue; Tadahiro Shimada; Hisaya Nabeshima; Hiroyoshi Sato; Keiichi Uchikawa, all of Yokohama, Japan

[73] Assignee: Shiseido Co., Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/793,864

[22] PCT Filed: Jul. 12, 1996

[86] PCT No.: PCT/JP96/01940

§ 371 Date: Apr. 16, 1997

§ 102(e) Date: Apr. 16, 1997

[87] PCT Pub. No.: WO97/02803

PCT Pub. Date: Jan. 30, 1997

[30] Foreign Application Priority Data

Jul. 12, 1995 [JP] Japan .................................. 7-199103
Sep. 29, 1995 [JP] Japan .................................. 7-276831
Sep. 30, 1995 [JP] Japan .................................. 7-276345

[51] Int. Cl.$^6$ .................................................. A61K 7/00
[52] U.S. Cl. ........................... 514/458; 514/643; 514/725
[58] Field of Search ..................... 514/458, 643, 514/725

[56] References Cited

U.S. PATENT DOCUMENTS 4,000,276 12/1976 Hasunuma et al. .
4,490,355 12/1984 Desai .
5,384,115 1/1995 Bissett et al. ............................. 424/59
5,580,549 12/1996 Fukuda et al. ............................. 424/62

FOREIGN PATENT DOCUMENTS 0 203 750   12/1986   European Pat. Off. .
06293625A  10/1994   Japan .
WO 92 19216 11/1992   WIPO .
WO 92 19218 11/1992   WIPO .
WO 92 19275 11/1992   WIPO .

OTHER PUBLICATIONS

CTFA Cosmetic Ingredient Dictionary, pp. 271, 374, 1982.
CA 121: 186797, Uno et al, May 10, 1994.

*Primary Examiner*—Rebecca Cook
*Attorney, Agent, or Firm*—Snider & Chao, LLP; Fei-Fei Chao; Ronald R. Snider

[57] ABSTRACT

The purpose of the present invention is to provide the external preparation for skin sufficiently exhibits a moisturizing function and skin improvement function of a specific quaternary ammonium salt.

Therefore, the external preparation for skin in accordance with the present invention comprising a quaternary ammonium salt which is shown in following constitutional formula (I), has an enhancer of moisturizing effect and skin roughness improvement effect of a quaternary ammonium salt selected from the group of vitamin E types, vitamin A derivatives, and alkyl denatured carboxyvinyl polymer.

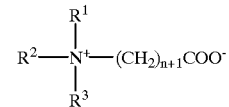

(I)

(wherein $R^1$, $R^2$, and $R^3$ show alkyl groups having a carbon number from 1 to 6. A sum total of the carbon number of $R^1$, $R^2$, $R^3$, and n is 8 or less. Each carbon number of $R^1$, $R^2$, and $R^3$ can be same or different).

12 Claims, No Drawings

EXTERNAL PREPARATION FOR SKIN CONTAINING A LOW-MOLECULAR-WEIGHT BETAINE

This application claims the priority of PCT application JP 96/01940, filed on Jul. 12, 1996.

TECHNICAL FIELD

The present invention relates to an external preparation for skin and in particular, relates to an enhancer of betaine which has a moisturizing function and a skin improvement function.

BACKGROUND ART

A maintenance function of a beautiful skin state is one of the fundamental functions of an external preparation for skin such as cosmetics. In order to maintain this beautiful skin state, it is essential to condition the sulci cutis and cristae of the skin by preventing or improving a skin roughness.

In order to attain this object, various humectants such as glycerin, sorbitol, propylene glycol, polysaccharide, and the like have been compounded into cosmetics.

However, among these humectants, e.g., polysaccharide may cause precipitation in the formulation which contains a large amounts of alcohol. Cosmetics which are compounded with glycerin, sorbitol, propylene glycol, and the like in large amounts for the purpose of improving the moisturizing effect, have a tendency to be attended with the sticky feel of use.

In order to remove the sticky feel of use of the cosmetics which is attendant to the improvement of the moisturizing effect, an experiment of compounding trimethylglycine (quaternary ammonium salt) into a cosmetic has been done (cf. Japanese Unexamined Patent Publication Hei No. 6-293625).

A cosmetic which is compounded with trimethylglycine independently can reduce the sticky feel of use. However, in the case where trimethylglycine is compounded in the dosage which is enough to exhibit the improvement effect of the skin state that trimethylglycine is possessed, such an external preparation for skin has a tendency to be attended with "powdery feel of use" by the presence of trimethylglycine. Therefore, the external preparation for skin which is compounded trimethylglycine independently, does not sufficiently satisfy the requirements of users.

DISCLOSURE OF INVENTION

In view of the above-mentioned problem of the prior art, the object of the present invention is to provide an external preparation for skin which can sufficiently exhibit the moisturizing function and the skin improvement function of trimethylglycine.

As the result of diligent studies of the inventors for attaining the above-mentioned object, it has been found that coexistence with a specific high-molecular components or vitamins, can largely improve the moisturizing function and the skin improvement function that the low-molecular-weight betaine is normally possessed. Accordingly, the present invention has been accomplished.

Namely, the present invention provides an external preparation for skin comprising a quaternary ammonium salt which is shown by following constitutional formula (I), and, an enhancer of the moisturizing function, and the skin improvement function of a quaternary ammonium salt selected from the group consisting of vitamin E types, vitamin A derivatives, and alkyl denatured carboxyvinyl polymer.

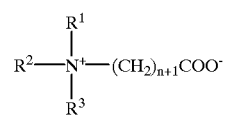

(I)

(wherein $R^1$, $R^2$, and $R^3$ show alkyl groups having a carbon number from 1 to 6. A sum total of the carbon number of $R^1$, $R^2$, $R^3$, and n is 8 or less. Each carbon number of $R^1$, $R^2$, and $R^3$ can be same or different.)

Preferably, the compounding amount of the quaternary ammonium salt is in the range from 0.1% by weight to 30% by weight with respect to the whole amount of the external preparation.

More preferably, the compounding amount of the quaternary ammonium salt is in the range from 0.1% by weight to 20% by weight with respect to the whole amount of the external preparation.

Preferably, vitamin E types are tocopherol and/or vitamin E acetate.

Also preferably, the compounding amount of the vitamin E types is in the range from 0.0001% by weight to 2.0% by weight with respect to the whole amount of the external preparation.

More preferably, the compounding amount of the vitamin E types is in the range from 0.001% by weight to 0.5% by weight with respect to the whole amount of the external preparation.

Preferably, vitamin A derivatives are vitamin A ester.

Also preferably, the compounding amount of the vitamin A derivatives is in the range from $1\times10^{-5}$% by weight to 5.0% by weight with respect to the whole amount of the external preparation.

Further preferably, the compounding amount of the vitamin A derivatives is in the range from $1\times10^{-4}$% by weight to 0.5% by weight with respect to the whole amount of the external preparation.

Preferably, the compounding amount of the alkyl denatured carboxyvinyl polymer is in the range from 0.01% by weight to 5.0% by weight with respect to the whole amount of the external preparation.

More preferably, the compounding amount of the alkyl denatured carboxyvinyl polymer is in the range from 0.05% by weight to 2.0% by weight with respect to the whole amount of the external preparation.

In the following, the constitution of the present invention will be explained in further detail.

Quaternary Ammonium Salt

Firstly, it will be explained about quaternary ammonium salt which is characteristic in the present invention.

A quaternary ammonium salt which is shown in constitutional formula (I) and compounded with the external preparation for skin of the present invention is a mode of the molecule which is generally called "betaine".

In formula (I), $R^1$, $R^2$, and $R^3$ show alkyl groups having a carbon number from 1 to 6. And also, a sum total of the carbon number of $R^1$, $R^2$, and $R^3$ and n (which is integer 0 or more) is 8 or less.

If the sum total of the carbon number becomes 9 or more, and the molecular weight of the part of nitrogen atom and the alkyl groups ($R^1$, $R^2$, and $R_3$) which is combined with this nitrogen atom becomes relatively large in a quaternary ammonium salt (I), the hydrophobic nature of the above-mentioned part is increased. This is not preferred since the property of the quaternary ammonium salt as an amphoteric surfactant tend to be actualized.

As for the Alkyl groups having a carbon number from 1 to 6, the straight chain alkyl group or branched chain alkyl group of said carbon number can be widely applied. Namely, a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group, an isohexyl group, a 3-methylpentyl group, a 2,2-dimethylbutyl group, a 2,3-dimethylbutyl group, and the like can be exemplified as the alkyl group which has said carbon number.

And, the carbon number of $R^1$, $R^2$, and $R^3$ can be same or different.

As for the combination of the alkyl groups, in the tendency to reduce the property of the quaternary ammonium salt as an amphoteric surfactant as much as possible, it is preferable to decrease the carbon number of $R_1$, $R_2$, and $R_3$ as little as possible. Therefore, it is preferable in the case where the combination of all alkyl groups of the quaternary ammonium salt (I) are methyl groups at the same time, and n is 0, namely, it is more preferable to compound trimethylglycine or γ-butyrobetaine (that all alkyl groups are methyl groups at the same time and n is 2) as a quaternary ammonium salt. And also, trimethylglycine and γ-butyrobetaine are known to be widely distributed in the animal and vegetable kingdoms, and they are the preferable quaternary ammonium salt for planning a physiologically beautiful skin state as much as possible.

Vitamin E Types

Next, it will be explained about vitamin E types which can synergistically enhance the moisturizing function and the skin improvement function of the quaternary ammonium salt by combining it with the quaternary ammonium salt.

Examples of the vitamin E types which can be compounded for the external preparation of the present invention are selected from vitamin E such as natural vitamin E, α-tocopherol, β-tocopherol, γ-tocopherol, δ-tocopherol; vitamin E derivatives such as vitamin E acetate, vitamin E nicotinate, α-tocopherol-2, L-ascorbic acid phosphate diester; the salt of these, and the like.

These examples of vitamin E types listed here are comprised of, needless to say d-isomer which ordinarily exists in nature, and optical isomers that can be synthesized such as l-isomer, or dl-isomer which is the mixture of d-isomer and l-isomer. In the case where we are referring to vitamin E types in the present invention, unless otherwise stated, it comprises all these possibilities.

Further, if the external preparation has a formulation form which is desired to be transparent (e.g., water solution type or solubilization type), it is preferable to compound the water soluble vitamin E derivatives by selecting from among these vitamin E types, in view of making the transparency better.

The vitamin E types listed here can be synthesized by the publicly known methods (e.g., Trost method) and can also use vitamin E purchased in the market.

In the external preparation for skin of the present invention, if vitamin E types are used as an enhancer of moisturizing function and skin improvement function, the compounding amount of the above- mentioned quaternary ammonium salt (I) is preferably in the range from 0.01% by weight to 30% by weight, and more preferably in the range from 0.1% by weight to 20% by weight with respect to the whole amount of the external preparation. In case of compounding a quaternary ammonium salt into a skin lotion, by compounding about 8.0% by weight of the quaternary ammonium salt, the sufficient effect can be exhibited. In the case where the compounding amount is less than 0.01% by weight, the moisturizing function and the skin improvement function of the quaternary ammonium salt becomes insufficient, and it cannot sufficiently control the stickiness which is caused by the addition of other humectants. Also, even though a quaternary ammonium salt is compounded with 30% by weight or more, the effective increase which corresponds to the increase of the compounding amount cannot be expected. The feel of use of external preparation for skin which is compounded with such an excessive amount of the quaternary ammonium salt (I) is powdery and is not preferable because of the deteriorating of suitability for skin.

Also, if the quaternary ammonium salt (I) is compounded in the range from 0.01% by weight to 1% by weight with respect to the whole amount of the external preparation for skin, it generally exhibits the moisturizing function and skin improvement function of the quaternary ammonium salt (I). However, it sometimes cannot sufficiently control the sticky feel of use, according to the property of other humectants with which it coexists.

Further, if the quaternary ammonium salt (I) is compounded in the range from 20% by weight to 30% by weight with respect to the whole amount of the external preparation for skin in accordance with the present invention, a specific powdery feel of use is possible by compounding of this quaternary ammonium salt (I), according to the formulation form.

Preferably, the compounding amount of the vitamin E types which are compounded to the external preparation for skin in accordance with the present invention is in the range from 0.0001% by weight to 2.0% by weight with respect to the whole amount of the external preparation for skin (hereinafter, when this application refers to as "preferable compounding range", as shown in here, it means the preferable compounding range of the compounding ingredients for the external preparation for skin of the present invention). More preferably, the compounding amount of the vitamin E types is in the range from 0.001% by weight to 0.5% by weight with respect to the whole amount of the external preparation for skin (hereinafter, when this application refers to as "optimum compounding range", as shown in here, it means the more preferable compounding range of the compounding ingredients of the external preparation for skin in accordance with the present invention).

If the compounding amount of the vitamin E types is less than 0.0001% by weight, it is not preferable because the enhancement actions of moisturizing function, skin roughness improvement function, and skin roughness protecting function of the quaternary ammonium salt is not sufficiently exhibited.

And also, if vitamin E types are compounded with more than 2.0% by weight, the enhancement action which corresponds to the compounding amount of vitamin E cannot be observed. Further, an excessive amount of vitamin E as stated above causes oxidation with the passage of time, and it is not preferable because of the adverse effect of deteriorated vitamin E types caused by this oxidation, e.g., offensive odor sometimes occurs in a comparatively short period of time.

And further, in the case where the compounding amount of the vitamin E types is in the range from 0.0001% by weight to 0.001% by weight with respect to the whole amount of the external preparation for skin, the enhancement actions of the quaternary ammonium salt can be observed.

However, for the purpose of exhibiting the enhancement effect sufficiently, it need to be take into account of making the compounding amount of the quaternary ammonium salt enlarge relatively. In this case, it cannot deny a possibility of being accompanied this specific powdery feel of use of the quaternary ammonium salt according to this formulation form.

And, in the case where the compounding amount of the vitamin E types is in the range from 0.5% by weight to 2.0% by weight with respect to the whole amount of the external preparation for skin, the enhancement actions of the skin roughness protecting function and skin roughness improvement function can be observed, there is also a possibility of being made sticky by the vitamin E types which is compounded therein according to the formulation form of the external preparation for skin.

Each vitamin E types stated above can be compounded separately, and also can be compounded by combining properly.

The combination ratio of the vitamin E types is not limited as long as the compounding amount of the vitamin E types to the external preparation for skin is not deviated from the above-mentioned compounding amounts, it can be combined with discretionary ratios.

The compounding ratio between the vitamin E types and the quaternary ammonium salt is not limited as long as both of the ingredients are compounded within the preferable compounding range, and it can control properly according to the concrete formulation form. However, in the case where the one component is compounded too much and the other is compounded a little, even within the preferable compounding range, it cannot deny the tendency that the property of only one side of the compounding ingredients are reflected excessively in the external preparation for skin of the present invention.

By compounding the quaternary ammonium salt (I) with the vitamin E types to the external preparation for skin, the effect of the quaternary ammonium salt (I) can be maintained which controls the sticky feel of use by the addition of other compounding ingredients such as humectants, and further can improve moisturizing effect, skin roughness improvement effect, and skin roughness protecting effect synergistically. Namely, even though the quaternary ammonium salt (I) is not compounded excessively as to produce the powdery feel of use, to the external preparation, it can provide the external preparation for skin which is given enough moisturizing effect, skin roughness improvement effect, and skin roughness protecting effect.

Vitamin A Derivatives

Next, it will be explained that vitamin A derivatives which, as like the above-mentioned vitamin E types, can synergistically enhance moisturizing function and skin roughness improvement function of the quaternary ammonium salt by being combined with the quaternary ammonium salt.

The vitamin A derivatives which can be compounded with the external preparation of the present invention are selected from vitamin A esters such as vitamin A palmitate, vitamin A acetate, and the like. However, said vitamin A derivatives are not limited to these listed above. For example, retinol or ether of vitamin A and saccharide as vitamin A derivatives can be compounded with the external preparation for skin in accordance with the present invention.

However, in considering the stability and the like within the external preparation for skin, vitamin A esters are preferable.

Each of vitamin A derivatives listed here can be synthesized by the normally and publicly known methods, and can be used the goods in the market.

Further, these vitamin A derivatives have already been widely compounded with external preparations for skin, e.g., for the purposes of protecting the dryness of epidermis and correcting the abnormality of a keratinization. The safety of the vitamin A derivatives within the external preparation for skin is already confirmed.

In the external preparation for skin in accordance with the present invention, in the case where the vitamin A derivatives are used as an enhancer for moisturizing function and skin improvement function of the quaternary ammonium salt, preferably, the compounding amount of the quaternary ammonium salt is in the range from 0.01% by weight to 30% by weight, and more preferably, is in the range from 0.1% by weight to 20% by weight with respect to the whole amount of the external preparation for skin. In the case where the compounding amount of the quaternary ammonium salt is less than 0.01% by weight with respect to the whole amount of the external preparation for skin, the moisturizing function and the skin improvement function of the quaternary ammonium salt become insufficient and the stickiness caused by the addition of other humectants and the like cannot be sufficiently controlled. Also, in the case where the quaternary ammonium salt is compounded more than 30% by weight with respect to the whole amount of the external preparation, the increase of the effect which corresponds to the increase of the compounding amount cannot be expected. And further, the feel of use of external preparation for skin which is compounded with an excessive amount of the quaternary ammonium salt (I) is not preferable because it becomes powdery and unsuitable for skin.

In the case where the quaternary ammonium salt (I) is compounded in the range from 0.01% by weight to 1% by weight with respect to the whole amount of the external preparation for skin, moisturizing function and skin improvement function of the quaternary ammonium salt (I) can be exhibited, but the stickiness feel of use cannot be sufficiently controlled according to the property of the humectants which coexists in the external preparation.

Further, in the case where the quaternary ammonium salt (I) is compounded in the range from 20% by weight to 30% by weight with respect to the whole amount of the external preparation for skin in accordance with the present invention, it may have the specific powdery feel of use by compounding of this quaternary ammonium salt (I), according to the formulation form of the external preparation for skin of the present invention.

Preferably, the compounding amount of the vitamin A derivatives is in the range from $1 \times 10^{-5}$% by weight to 5.0% by weight (hereinafter referred to as "preferable compounding range"). More preferably, the compounding amount of the vitamin A derivatives is in the range from $1 \times 10^{-4}$% by weight to 0.5% by weight (hereinafter, referred to as "optimum compounding range") with respect to the whole amount of the external preparation for skin.

In the case where the compounding amount of the vitamin A derivatives is less than $1 \times 10^{-5}$% by weight, it is not preferable because the expected effects by compounding vitamin A derivatives, namely an enhancement actions of moisturizing function, skin roughness improvement function, and skin roughness protecting function of the quaternary ammonium salt are not sufficiently exhibited.

Even if the vitamin A derivatives are compounded more than 5.0% by weight, the improvement of the enhancement effects which corresponds to the increase of the compounding amount are not observed. Further, an excess amount of the vitamin A derivatives causes oxidation with the passage of time, and it is not preferable because of the adverse effect of deteriorated vitamin A derivatives caused by this oxidation, e.g., offensive odor sometimes occurs in a comparatively short period of time.

Further, in the case where the compounding amount of the vitamin A derivatives is in the rage from $1 \times 10^{-5}\%$ by weight to $1 \times 4^{-4}\%$ by weight with respect to the whole amount of the external preparation for skin, the above-mentioned effects can be observed. However, in order to sufficiently exhibit the above-mentioned effect, it needs to be taken into account of making the compounding amount of the quaternary ammonium salt enlarge relatively. In this case, according to the formulation form of the external preparation for skin, it cannot deny the possibility of being accompanied the specific powdery feel of use of the quaternary ammonium salt.

In the case where the compounding amount of the vitamin A derivatives is in the range from 0.5% by weight to 5.0% by weight with respect to the whole amount of the external preparation for skin, the improvement of skin roughness protecting effect and skin roughness improvement effect can be observed. There is a possibility of being sticky by the compounded vitamin A derivatives according to this formulation form of the external preparation for skin.

Also, each of the vitamin A derivatives stated above can be compounded separately into the external preparation for skin, and also can be compounded by combining them properly.

The combination ratio of these vitamin A derivatives is not limited as long as the compounding amount of the vitamin A derivatives to the external preparation for skin is not over the above-mentioned compounding amounts, they can be combined by a discretionary ratio.

The compounding ratio of the vitamin A derivatives and the quaternary ammonium salt (I) is not limited as long as both of the ingredients are compounded within the above-mentioned preferable compounding range, and it can be adjusted according to its concrete formulation form. However, in the case where the one ingredient is compounded too much, and the other is compounded too a little, even within the preferable compounding range, it cannot deny the tendency that the property of only one side of the compounding ingredient is reflected excessively in the external preparation for skin of the present invention.

By compounding the quaternary ammonium salt (I) together with the vitamin A derivatives to the external preparation for skin, the effect of the quaternary ammonium salt (I) can be maintained which controls the sticky feel of use by the addition of other compounding ingredients such as humectants, and further can improve moisturizing effect, skin roughness improvement effect, and skin roughness protecting effect synergistically. Namely, even though the quaternary ammonium salt (I) is not compounded excessively until it produces the powdery feel of use, to the external preparation, it can provide the external preparation for skin which is sufficiently given moisturizing effect, skin roughness improvement effect, and skin roughness protecting effect.

Alkyl Denatured Carboxyvinyl Polymer

The alkyl denatured carboxyvinyl polymer which is used in the present invention is acrylate alkyl methacrylate copolymer, and can be manufactured by normal methods. To be concrete, this alkyl denatured carboxyvinyl polymer is placed on the market as CARBOPOL 1342 (Produced by United States of America B.F. Goodrich Chemical Company Registered Trademark), PEMULEN TR-1 (same as above), PEMULEN TR-2 (same as above), and the like. These are commercially available.

In the present invention, preferably, the quaternary ammonium salt used together with the alkyl denatured carboxyvinyl polymer is compounded in the range from 0.01 to 30% by weight, and more preferably, is compounded in the range from 0.1 to 20% by weight with respect to the whole amount of the composition of the present invention. In the case where the compounding amount of the quaternary ammonium salt is less than 0.01% by weight, the moisturizing effect and the skin improvement effect of the quaternary ammonium salt is not sufficiently exhibited. And even if the quaternary ammonium salt is compounded more than 30% by weight, the increase of the effect which corresponds to the increase of the compounding amount is not expected.

In the present invention, preferably, the alkyl denatured carboxyvinyl polymer is compounded in the range from 0.01 to 5% by weight, and more preferably, is compounded in the range from 0.05 to 2% by weight with respect to the external preparation for skin of the present invention. If the compounding amount is less than 0.01% by weight, the moisturizing effect and the skin improvement effect are not sufficiently exhibited. And in the case where the compounding amount is more than 5% by weight, the viscosity of the composition becomes too high and it sometimes stand out clearly the stickiness with a view of the usability.

In particular, in the case where comparative low concentration quaternary ammonium salt and alkyl denatured carboxyvinyl polymer are compounded, namely, in the case where the compounding amount of the quaternary ammonium salt is less than 10% by weight and the compounding amount of the alkyl denatured carboxyvinyl polymer is less than 0.1% by weight, it exhibits relative low viscosity, an excellent moisturizing effect, and a skin improvement effect like the cases which use the vitamin E types and the vitamin A derivatives.

On the other hand, if the compounding amount of the quaternary ammonium salt is more than 10% by weight and the compounding amount of the alkyl denatured carboxyvinyl polymer is more than 0.1% by weight, the system is in a tendency to form gel. However, it is hard to yield the "powdery feeling" of the quaternary ammonium salt relatively, and it is the preferable system in the particular case where is inclined to use the quaternary ammonium salt at high concentrations.

Namely, in the case where the alkyl denatured carboxyvinyl polymer is used as the base of gel state products in the field of cosmetics and drugs, it is necessary to neutralize the alkyl denatured carboxyvinyl polymer by basic substance in order to obtain the gel composition. In addition to this, in order to obtain the gel composition which is further given moisturizing effect and skin roughness improvement effect, it has to have added a humectant such as glycerin and other ingredients. Accordingly, in case of making a gel base which has a proper viscosity and also has moisturizing effect and skin roughness improvement effect, it leads to increase the number of the manufacturing process steps, and it also has a problem of being a complicated process of manufacturing.

As compared with this, by using the alkyl denatured carboxyvinyl polymer together with the quaternary ammonium salt, as like the present invention, it does not have to neutralize said alkyl denatured carboxyvinyl polymer by basic substance and it also can exhibit moisturizing effect and skin roughness improvement effect.

Other Ingredients

In the present invention, by using vitamin E types, vitamin A derivatives, alkyl denatured carboxyvinyl polymer, and a quaternary ammonium salt (I) as the mixture of the bases which corresponds to the expected formulation form and can be permitted in the preparation, it is possible to exhibit the expected effect of the present invention of "offering the external preparation for skin which is excellent in moisturizing effect, skin roughness improvement effect, skin roughness protecting effect, and feeling of use". There is no particular necessity to compound other additional ingredients, as long as the external preparation for skin is the only intended use of these expected effects.

However, to compound other ingredients for the purpose of giving the effects that the external preparation for skin will generally acts, is possible as long as the expected effects of the present invention are not spoiled by this compounding.

For example, in case of intending the external preparation for skin which is further given a moisturizing effect, it can be compounded with moisturizing ingredients such as polyethylene glycol, dipropylene glycol, 1,3-butylene glycol, glycerine, sorbitol, xylitol, maltitol, hyaluronic acid, sodium lactate, sodium PCA, chondroitin sulfate, Spanish mackerel extract, peony extract, rumex japonicus houtt, and the like.

In obtaining an external preparation for skin which is given a whitening effect, it can be compounded with a whitening ingredients of vitamin C such as arbutin, kojic acid or ascorbic acid, ascorbyl sulfate (salt), ascorbyl phosphate (salt), ascorbyl dipalmitate, and the like.

In obtaining an external preparation for skin which is further given a skin roughness protecting effect, it can be compounded with the ingredients which have a skin roughness protecting action. The ingredients are selected from an anti-inflammatory ingredients such as allantoin, glycyrrhizinic acid (salt), glycyrrhetinic acid and its derivatives, glutathione, acyl sarcosinate, tranexamic acid, saponins (e.g., saiko saponin, carrot saponin, sponge cucumber gourd saponin, and the like), glycyrrhiza extract, Japanese coptis extract, shikon extract, yarrow extract, comfrey extract, aloe extract, sorrel extract, nuphar extract, mallow extract, Japanese angelica extract, horsetail extract, saxifrage extract, arnica extract, extract of liliaceae vegetables, mugwort extract, gardenia extract, wild thyme extract, and the like; astringent ingredient such as citric acid, malic acid, tartaric acid, orange/ bitter orange peel/birch extract, hamamelis extract, white nettle extract, birch bark extract, rhubarb extract; vitamins such as vitamin A, vitamin B (e.g., vitamin $B_6$ hydrochloride, vitamin $B_6$ tripalmitate, vitamin $B_6$ dioctanoate, vitamin $B_2$ and its derivatives, vitamin $B_{1\ 2}$, vitamin $B_{1\ 5}$ and its derivatives, and the like), vitamin D, vitamin H, pantothenic acid, pantethine, nicotinamide, and the like; natural products extract such as ginseng extract, lilly extract, sponge cucumber gourd extract, human placental extract and the like.

In obtaining an external preparation for skin which is given a vasodilating effect, it can be compounded with vasodilating ingredients such as swertia herb extract, cnidium rhizome extract, sage extract, cephalanthin, γ-oryzanol, benzyl nicotinate, and the like.

In obtaining the external preparation for skin which is given an antibacterial effect, it can be compounded with antibacterial ingredients such as hinokitiol, bisabolol, eucalyptol, and the like.

In obtaining the external preparation for skin which is given a sebum inhibitory effect, it can be compounded with sebum inhibitory ingredients such as ethynylestradiol, and the like.

And, the ingredients which can be compounded in the external preparation for skin of the present invention, are not limited to these ingredients listed above. And also, the pharmaceutical effects which correspond to the above-listed ingredients, are not limited to these pharmaceutical effects. For example, vitamin C can be used as a whitening ingredient, and it also can be used as assistant antioxidants which will be described later. Further, the ingredients which are mentioned above are, except for compounding into the external preparation for skin separately, may be compounded by combining properly more than two kinds of pharmaceutical effect ingredients according to its object.

The external preparation for skin in accordance with the present invention is widely applicable to cosmetic ingredients, drugs, and quasi drugs, which are applied to the epidermis. And the formulation form is widely formable such as a water solution type, a solubilization type, an emulsification type, a powder type, an oily liquid type, a gel type, an ointment type, an aerosol type, a water-oil 2 phase type, a water-oil-powder 3 phase type, and the like. Namely, as for fundamental cosmetics, the external preparation for skin of the present invention can be used as a washing foam, a skin lotion, a milky lotion, a cream, a gel, an essence (skin lotion), a pack mask, and a cosmetic preparation for shaving. And as for make up cosmetics, the external preparation of the present invention is widely suitable for the form such as foundation, rouge, and the like. And further, as for drugs or quasi-drugs, the external preparation of the present invention is widely applicable to the form such as various ointment agent, and the like. However, the external preparation for skin in accordance with the present invention is not limited to these forms or formulation forms.

In the external preparation for skin in accordance with the present invention, normally and publicly known base ingredients can be widely compounded to the external preparation according to the expected forms and formulation forms as long as the compounding of the ingredients does not spoil the effects of the present invention. In particular, in case of compounding oily base ingredients to the external preparation for skin, it is desirable to compound within the range that the specific stickiness of the base ingredients does not spoil the feel of use of the external preparation for skin in accordance with the present invention.

The ingredients which are mentioned above are exemplified such as fats and oils, wax esters, ester oil, hydrocarbon oil, silicone, surfactant, lower alcohol, sterol, humectant, water-soluble high polymer, ultraviolet absorbers, sequestering agents, pH adjustor, neutralizer, antioxidants, antibacterial agents, pharmaceutical preparations, various extracts, and the like.

Namely, as for powder ingredients, titanium dioxide, mica, talc, kaolin, mica coated with titanium dioxide, and the like are exemplified.

As for fats and oils, liquid oils and fats such as linseed oil, camellia oil, macadamia nut oil, corn oil, mink oil, olive oil, avocado oil, sasanqua oil, castor oil, safflower oil, apricot kernel oil, cinnamon oil, jojoba oil, grape seed oil, sunflower seed oil, almond oil, rape seed oil, sesame oil, wheat germ oil, rice germ oil, rice bran oil, cottonseed oil, soybean oil, peanut oil, tea oil, evening primrose oil, egg yolk oil, beef leg oil, cod liver oil, triglycerin, trioctanoic acid, glycerine, glyceryl triisopalumitate, and the like; liquid or solid fats and oils such as coconut oil, palm oil, palm kernel oil, and the like; solid fats and oils such as cacao butter, beef tallow, mutton tallow, lard, horseflesh tallow, hydrogenated oil, hydrogenated castor oil, Japan wax, shea butter, and the like are exemplified.

As for hydrocarbon oils, oily components such as liquid paraffin, ozokerite, squalane, squalene, pristane, paraffin, isoparaffin, ceresin, petrolatum, microcrystalline wax, and the like are exemplified.

As for wax esters, beeswax, candelilla wax, cotton wax, carnauba wax, bayberry wax, Chinese wax, spermaceti, montan wax, rice bran wax, lanolin, hydrogenated lanolin, hard lanolin, kapok wax, sugarcane wax, jojoba wax, shellac wax, and the like are exemplified.

As for higher alcohols, cetanol, stearyl alcohol, isostearyl alcohol, 2-octyldodecanol, lanolin alcohol, and the like are exemplified.

As for higher fatty acids, lauric acid, myristic acid, palmitic acid, stearic acid, behenic acid, isostearic acid, oleic acid, linolenic acid, linoleic acid, hydroxystearic acid, and the like are exemplified.

As for ester oils, esters of octanoic acid such as cetyl octanoate and the like; esters of isooctanoic acid such as glyceryl tri(2-ethyl hexanoate), pentaerythritol tetra(2-ethylhexanoate), and the like; esters of lauric acid such as hexyl laurate, and the like; esters of myristic acid such as isopropyl myristate, 2-octyldodecyl myristate, and the like; esters of palmitic acid such as octyl palmitate, and the like; esters of stearic acid such as isocetyl stearate, and the like; esters of isostearic acid such as propyl isostearate, and the like; esters of isopalmitic acid such as octyl isopalmitate, and the like; esters of oleic acid such as isodecyl oleate, and the like; esters of adipic acid such as diisopropyl adipate, and the like; diesters of sebacic acid such as diethyl sebacate, and the like; diisostearyl malate, and the like are exemplified.

As for polar oils, diethylene glycol monopropyl ether, polyoxyethylene polyoxypropylene pentaerythritol ether, polyoxypropylene butyl ether, ethyl linoleate, and the like are exemplified.

As for silicones, chain silicones such as dimethyl polysiloxane, methylphenyl polysiloxane, methyl hydrogen polysiloxane, and the like; cyclic silicones such as octamethyl tetrasiloxane, decamethyl cyclopentasiloxane, dodecamethyl cyclohexasiloxane, and the like, are exemplified.

As for water-soluble thickening agents, vegetable type water-soluble high polymer such as arabic gum, tragacanth gum, galactene, carob bean gum, guar gum, xanthan gum, caraya gum, carrageenan, pectin, agar, quince seed (quince), algae choloid (algae extract), and the like; microbe type water-soluble high polymer such as dextran, succinoglucan, pullulan, and the like; animal type water-soluble high polymer such as collagen, casein, albumen, gelatin, and the like; cellulose type water-soluble high polymer such as methyl cellulose, nitrocellulose, ethyl cellulose, methylhydroxypropyl cellulose, hydroxyethyl cellulose, sodium cellulose sulfate, hydroxypropylcellulose, sodium carboxymethyl cellulose (CMC), microcrystalline cellulose, cellulose powder, and the like; alginic acid type water-soluble high polymer such as sodium alginate, propylene glycol alginate, and the like; vinyl type water-soluble high polymer such as polyvinyl alcohol, polyvinylmethyl ether, polyvinyl pyrrolidone, and the like; polyoxyethylene type water-soluble high polymer such as polyethylene glycol, and the like; copolymerization type water-soluble high polymer such as polyoxyethylene polyoxypropylene copolymer, and the like; acryl type water-soluble high polymer such as polyethylacrylate, polyacrylamide, and the like; Inorganic type water-soluble high polymer such as polyethyleneimine, cationic polymer, bentonite, aluminum magnesium silicate (bea gum), montmorillonite, laponite, hectorite, silicic anhydride, and the like are exemplified.

As for lower alcohols, methanol, ethanol, propyl alcohol, isopropyl alcohol, and the like are exemplified.

As for sterols, cholesterol, β-sitosterol, phytosterol, lanosterol, and the like are exemplified.

As for antioxidants or assistant antioxidants, butylhydroxy toluene, tocopherol, butylhydroxyanisol, gallic acid ester, phytic acid, malic acid, and the like are exemplified.

As for antibacterial agents, benzoic acid, salicylic acid, sorbic acid, carbolic acid, p-hydroxybenzoic acid alkyl ester (methylparaben, ethylparaben, butylparaben, and the like), benzalkonium chloride, chlorhexidine chloride, trichlorocarbanilide, photosensitizing dye, phenoxyethanol, hexachlorophene, and the like are exemplified.

As for nonionic surfactants, sorbitan monolaurate, sorbitan sesquioleate, sorbitan trioleate, polyoxyethylene sorbitan monolaurate, polyethylene glycol monooleate, polyoxyethylene alkylether, polyglycol diester, lauroyl diethanolamide, fatty acid isopropanolamide, maltitol hydroxy fatty acid group ether, alkylated polysaccharide, alkylglucoside, sugar ester, pantothenyl ethylether, and the like are exemplified.

As for cationic surfactants, stearyl trimethyl ammonium chloride, benzalkonium chloride, lauryl amine oxide, and the like are exemplified.

As for anionic surfactants, sodium palmitate, sodium laurate, potassium lauryl sulfate, triethanolamine alkyl sulfate ether, turkey-red oil, linear dodecylbenzene sulfate, polyoxyethylene hydrogenated castor oil malate, acyl methyl taurate, and the like are exemplified.

As for ultraviolet absorbers, benzoic acid type ultraviolet absorbers such as p-aminobenzoic acid, and the like; anthranilic acid type ultraviolet absorbers such as methyl anthranilate, and the like; salicylic acid type ultraviolet absorbers such as octyl salicylate, phenyl salicylate, homomenthyl salicylate, and the like; cinnamic acid type ultraviolet absorbers such as isopropyl methoxycinnamate, octyl p-methoxycinnamate, 2-ethylhexyl 4-methoxycinnamate, glyceryl octanoate di-p-methoxycinnamate, 3,4,5-trimethoxycinnamate, 3-methyl-4-[methylenebis (trimethylsiloxy) silyl]butyl, and the like; benzophenone type ultraviolet absorbers such as 2,4-dihydroxybenzophenone, 2-hydroxy-4-methoxybenzophenone, 2-hydroxy-4-methoxybenzophenone-5-sulfonic acid, 2-hydroxy-4-methoxybenzophenone-5-sodium sulfonate, and the like; urocanic acid, ethyl urocnate, 2-phenyl-5-methylbenzoxazole, 2-(2'-hydroxy-5'-methylphenyl) benzotriazole, 4-tert-butyl-4'-methoxybenzoilmethane, and the like are exemplified.

And, neutralizers also can be compounded to the external preparation in accordance with the present invention. For example, 2-amino-2-methyl-1-propanol, 2-amino-2-methyl-1,3-propanediol, potassium hydroxide, sodium hydroxide, triethanolamine, sodium carbonate, and the like are exemplified.

As for sequestering agents, sodium EDTA, alanine, sodium EDTA (salt), sodium polyphosphate, sodium metaphosphate, phosphoric acid, and the like are exemplified.

As for pH adjustor, lactic acid, citric acid, glycollic acid, succinic acid, tartaric acid, dl-malic acid, potassium carbonate, sodium bicarbonate, ammonium bicarbonate, and the like are exemplified.

As for refrigerants, menthol, penny royal oil, peppermint oil, camphor, thymol, inositol, spinlantol, methyl salicylate, and the like are preferable.

According to the formulations which correspond to the expected formulation forms, pigments, fragrances, purified water, and the like can be compounded to the external preparation for skin in accordance with the present invention by combining properly.

Further, proper fragrances, pigments, and the like can be added to the external preparation for skin of the present invention as occasions demand.

BEST MODE FOR CARRYING OUT THE INVENTION

In the following, the more concrete examples of the present invention will be explained. However, the present invention is not limited to these examples. And, the every expression "% by weight" as used following means "% by weight" with respect to the whole amount of the external preparation for skin.

Firstly, the evaluation method of follow-mentioned examples will be explained.
Measurement of the Moisturizing Effect by Means of Water Evaporation Rate The measurement of the water evaporation rate has been done as the test for measuring the moisturizing effect.

After dropping 10 μl of sample water on 2.0 cm square filter paper (TOYO Filter Paper No.2), leaving this as it is at a temperature of 25° C. and relative humidity 50% the reduced weight is measured by a scale. On the assumption that the evaporation of water proceeds by linear expression, a water evaporation rate constant for each sample was found. If the weight of sample is W in time T, the evaporation rate of water is shown as, $$dw/dt = kw \text{ (k: water evaporation rate constant).} \quad \text{Formula 1}$$

In integrating the above-shown formula, $$\ln w = -kt + c \text{ (c: constant)} \quad \text{Formula 2x}$$

is found. Measuring wn in time tn, plotting ln wn to tn according to the formula shown as formula 2, finding water evaporation rate constant (k) from the slope of the straight line of linear function. As the vaporization of water becomes bigger, the more this water evaporation rate constant (k) becomes bigger. And, if the K is smaller, water content is more difficult to vaporize and the moisturizing effect is higher.
(Evaluation)
◎: Water evaporation rate constant (k) is less than 0.035
○: Water evaporation rate constant (k) is in the range from 0.035 to 0.038
Δ: Water evaporation rate constant (k) is in the range from 0.038 to 0.041
X: Water evaporation rate constant (k) is 0.041 or more The water evaporation rate constant (k) of ion-exchanged water is 0.043.
Skin Roughness Improvement Test An activator (sodium lauryl sulfate) 10% water solution was applied to some portions of the forearms of 10 males of a panel in 3 days, to intentionally make the skin rough. Next, applying the following-mentioned test sample liquid to the rough skin portion twice in a day and the skin surface state was measured by the replica method 5 days after starting application. The skin roughness improvement effect was evaluated by the comparison between the rough skin portion where the test sample was applied liquid and the rough skin portion where nothing was applied.
(Evaluation of Skin Roughness)

Observing of the prepared replica by light microscope, and evaluating the symptoms of skin roughness. Namely,
1) occurring horny layer exfoliation and erythema,
2) sulci cutis and cristae are unclear, and the texture of skin is uneven, and the like has been evaluated.
(Evaluation Standard)
Remarkably effective: The symptom of skin roughness is disappeared
Effective: The symptom of skin roughness is weakened
Slightly effective: The symptom of skin roughness is slightly weakened
No effect: It is not obtained any change in the symptom of skin roughness (Judgement)
◎: Where the ratio of remarkably effective, effective, and slightly effective in the examinees 80% or more
○: Where the ratio of remarkably effective, effective, and slightly effective in the examinees is in the range from 50% to 80%
Δ: Where the ratio of remarkably effective, effective, and slightly effective in the examinees is in the range from 30% to 50%
X: Where the ratio of remarkably effective, effective, and slightly effective in the examinees is less than 30%

TEST EXAMPLES 1–6

The skin lotion was prepared according to the formulations shown in Table 1, and the effectiveness of the external preparation for skin of the present invention was studied by doing the above-mentioned water retention test and skin roughness improvement test.

The skin lotion was manufactured by the ordinary process.

TABLE 1

| Test example | 1 | 2 | 3 | 4 | 5 | 6 |
|---|---|---|---|---|---|---|
| Ethanol | 5.0 | 5.0 | 5.0 | 5.0 | 5.0 | 5.0 |
| Polyoxyethylene oleylether (15 mol) | 0.8 | 0.8 | 0.8 | 0.8 | 0.8 | 0.8 |
| Methylparaben | 0.1 | 0.1 | 0.1 | 0.1 | 0.1 | 0.1 |
| Trimethylglycine | 2.0 | 2.0 | 2.0 | 2.0 | 2.0 | 2.0 |
| dl-α-tocopherol | 0.01 | — | — | — | — | — |
| Vitamin A palmitate | — | 0.01 | — | — | — | — |
| Alkyl denatured carboxyvinyl polymer | — | — | 0.01 | — | — | — |
| Carboxyvinyl polymer | — | — | — | 0.01 | — | — |
| Vitamin B$_6$ | — | — | — | — | 0.01 | — |
| Vitamin D | — | — | — | — | — | 0.01 |
| Purified water | balance | balance | balance | balance | balance | balance |
| Moisturizing effect | ◎ | ◎ | ◎ | ○ | Δ | Δ |
| Skin roughness improvement effect | ◎ | ◎ | ◎ | Δ | ○ | ○ |

As is clearly from the above-mentioned Table 1, by compounding dl-α-tocopherol (vitamin E types), vitamin A palmitate (vitamin A derivatives), and alkyl denatured carboxyvinyl polymer together with trimethylglycine (quaternary ammonium salt), both the moisturizing effect and skin roughness improvement effect are excellently exhibited. However, in the case where carboxyvinyl polymer (thickening agent, humectant) is compounded, it can be observed only in the moisturizing effect practically. And in case of compounding vitamin $B_6$ and vitamin D (vitamins which are supposed to possess the skin roughness improvement effect), it can be observed only in the skin roughness improvement effect.

Therefore, the inventors have paid attention to the above-mentioned vitamin E types, vitamin A derivatives, and alkyl denatured carboxyvinyl polymer, and further proceeded with the study.

Quaternary Ammonium Salt and Vitamin E Types

Firstly, the inventors have manufactured the skin lotion which is the following Table 2 and Table 3, by the basic formulation as like Table 1. And they further studied about the mutual relation between the quaternary ammonium salt and the vitamin E types.

TABLE 2

| Test example | 1-1 | 1-2 | 1-3 | 1-4 | 1-5 | 1-6 |
|---|---|---|---|---|---|---|
| Ethanol | 5.0 | 5.0 | 5.0 | 5.0 | 5.0 | 5.0 |
| Polyoxyethylene oleylether (15 mol) | 0.8 | 0.8 | 0.8 | 0.8 | 0.8 | 0.8 |
| Methylparaben | 0.1 | 0.1 | 0.1 | 0.1 | 0.1 | 0.1 |
| Trimethylglycine | 2.0 | 2.0 | 2.0 | 2.0 | 2.0 | 2.0 |
| dl-α-tocopherol | 0 | 0.0001 | 0.001 | 0.01 | 0.5 | 2.0 |
| Purified water | balance | balance | balance | balance | balance | balance |
| Moisturizing effect | Δ | ○ | ◎ | ◎ | ◎ | ◎ |
| Skin roughness improvement effect | Δ | Δ | ○ | ◎ | ◎ | ◎ |

In test examples 1-3 to 1-6 which is compounded trimethylglycine as a quaternary ammonium salt and dl-α-tocopherol as a vitamin E types with the optimum compounding range, the skin lotion is excellent in both moisturizing effect and skin roughness improvement effect. However, when preserving the skin lotion for a long period, when a large amount of dl-α-tocopherol over test example 1-6 was compounded to the skin lotion, it sometimes caused an offensive odor. So the compounding amount of dl-α-tocopherol was preferably less than 2.0% by weight.

Since the compounding amount of dl-α-tocopherol is relatively small, though the skin lotion of test examples 1-2 and 1-3 become slightly inconspicuous in skin roughness improvement effect as compared with the skin lotion of test examples 1-4 to 1-6. The skin lotion were worked sufficiently the expected effects of the present invention.

TABLE 3

| Test example | 1-7 | 1-8 | 1-9 | 1-10 | 1-11 | 1-12 | 1-13 |
|---|---|---|---|---|---|---|---|
| Ethanol | 5.0 | 5.0 | 5.0 | 5.0 | 5.0 | 5.0 | 5.0 |
| Polyoxyethylene oleylether (15 mol) | 0.8 | 0.8 | 0.8 | 0.8 | 0.8 | 0.8 | 0.8 |
| Methylparaben | 0.1 | 0.1 | 0.1 | 0.1 | 0.1 | 0.1 | 0.1 |
| Trimethylglycine | 0 | 0.01 | 0.1 | 8.0 | 10.0 | 20.0 | 30.0 |
| dl-α-tocopherol | 0.01 | 0.01 | 0.01 | 0.01 | 0.01 | 0.01 | 0.01 |
| Purified water | balance | balance | balance | balance | balance | balance | balance |
| Moisturizing effect | X | Δ | ○ | ◎ | ◎ | ◎ | ◎ |
| Skin roughness improvement effect | X | Δ | ○ | ◎ | ◎ | ◎ | ◎ |

As is clearly from Table 3, the skin lotion which is compounded 0.01% by weight or more of trimethylglycine can obtain moisturizing effect and skin roughness improvement effect, but its remarkable effect is only exhibited in the case where trimethylglycine is compounded 0.1% by weight or more to the skin lotion. In test example 1-8, the moisturizing effect can be improved by compounding other humectants additionally.

And, in the case where trimethylglycine is compounded 30.0% by weight or more to the skin lotion, the slight powdery feeling appeared.

From these test examples, it can be understood that the skin lotion which is compounded dl-α-tocopherol and trimethylglycine within the optimum compounding range is an excellent skin lotion which can sufficiently exhibit the expected effects.

And, it was also proved that the skin lotion which is compounded these within the preferable compounding range can work enough for practical use in view of exhibiting the expected effect.

Other vitamin E types except for dl-α-tocopherol which can be compounded to the external preparation for skin of the present invention is in common with dl-α-tocopherol in the fundamental pharmaceutical effects as a vitamin E types. Therefore, in case of compounding these other vitamin E types by the formulation which corresponds to the properties of each vitamin E types in place of dl-α-tocopherol, the excellent skin lotion as the test examples is provided.

Next, the milky lotion of the formulation in Table 4 was prepared, and the effectiveness of the external preparation for skin in accordance with the present invention was studied by doing the above-mentioned water retention test and skin roughness improvement test.

TABLE 4

| | Example | | | Comparative example | | |
|---|---|---|---|---|---|---|
| | 1 | 2 | 3 | 1 | 2 | 3 |
| (Oil phase) | | | | | | |
| Squalane | 10.0 | 10.0 | 10.0 | 10.0 | 10.0 | 10.0 |
| Petrolatum | 2.0 | 2.0 | 2.0 | 2.0 | 2.0 | 2.0 |
| Cetanol | 1.0 | 1.0 | 1.0 | 1.0 | 1.0 | 1.0 |
| Lanolin alcohol | 2.0 | 2.0 | 2.0 | 2.0 | 2.0 | 2.0 |

TABLE 4-continued

|  | Example | | | Comparative example | | |
| --- | --- | --- | --- | --- | --- | --- |
|  | 1 | 2 | 3 | 1 | 2 | 3 |
| Liquid paraffin | 8.0 | 8.0 | 8.0 | 8.0 | 8.0 | 8.0 |
| Vitamin E acetate | 0.01 | 0.001 | 0.01 | — | 0.01 | — |
| Antiseptic agent | 0.2 | 0.2 | 0.2 | 0.2 | 0.2 | 0.2 |
| Perfume (Water phase) | 0.05 | 0.05 | 0.05 | 0.05 | 0.05 | 0.05 |
| Carboxy vinyl polymer | 0.2 | 0.2 | 0.2 | 0.2 | 0.2 | 0.2 |
| Alkyl denatured carboxyvinyl polymer | 0.7 | 0.7 | 0.7 | 0.7 | 0.7 | 0.7 |
| KOH | 0.3 | 0.3 | 0.3 | 0.3 | 0.3 | 0.3 |
| Trimethyl- | 5.0 | 5.0 | 0.05 | 5.0 | — | — |
| Purified water | balance | balance | balance | balance | balance | balance |
| Moisturizing effect | ◉ | ◉ | Δ | Δ | X | X |
| Skin roughness improvement effect | ◉ | ○ | ○ | X | X | X |

(Process)

It was preemulsified by adding the heated and dissolved oil phase at 70° C. to the water phase of 70° C., and further uniformly emulsified by a homomixer. After this, it was cooled down to 30° C., and the milky lotion was obtained.

The milky lotion in accordance with the example 1 which are compounded the quaternary ammonium salt (trimethylglycine) and the vitamin E types (vitamin E acetate) within the optimum compounding range, are particular excellent in both moisturizing effect and skin roughness improvement effect.

Since the compounding amount of vitamin E acetate is relative small as compared with example 1, the milky lotion of the example 2 become inconspicuous in skin roughness improvement effect. But, the milky lotion worked sufficiently according to the expected effect of the present invention.

The milky lotion in accordance with the example 3 is slightly inferior in moisturizing effect. The moisturizing effect of trimethylglycine may not appear remarkably because that the compounding amount of trimethylglycine has not reached to the optimum compounding range (though the compounding amount of trimethylglycine is within the preferable compounding range). The moisturizing property can be improved by compounding other humectants to this milky lotion.

And, all the milky lotions of these examples have not been accompanied with the powdery feel of use.

In comparative example 1, though trimethylglycine was compounded to the external preparation for skin within the optimum compounding range, it was inferior in both moisturizing effect and skin roughness improvement effect. It is possible that the synergistic action caused by the compounding of the quaternary ammonium salt (I) and the vitamin E types is not exhibited, since the vitamin E types were not compounded at all.

Conversely, comparative example 2 which was compounded vitamin E acetate and was not compounded with any quaternary ammonium salt (I), did not exhibit the effect of the present invention as like comparative example 1.

And further, comparative example 3 which was not compounded with both the vitamin E types and the quaternary ammonium salt (I) (needless to say) did not exhibit the effect of the present invention.

In these examples and comparative examples, the milky lotion which was compounded vitamin E acetate as vitamin E types and trimethylglycine as quaternary ammonium salt (I) within the optimum compounding range, sufficiently exhibited the expected effect.

The milky lotion which was compounded vitamin E acetate (vitamin E types) and trimethylglycine (quaternary ammonium salt) within the preferable compounding range, was sufficiently fit for use, in view of the exhibition of the expected effect.

Other vitamin E types except for vitamin E acetate which can be compounded to the already-described external preparation for skin is in common with vitamin E acetate in the fundamental pharmaceutical effects as the vitamin E types. Therefore, in case of compounding these other vitamin E types by the formulation which corresponds to the properties of each vitamin E types in place of vitamin E acetate, the excellent milky lotion as like said examples can be provided.

Quaternary Ammonium Salt and Vitamin A Derivatives

Next, the inventors have manufactured the skin lotion shown in the following described Table 5 and Table 6, and the study further proceeded about the mutual relation between the quaternary ammonium salt and the vitamin A derivatives.

TABLE 5

| Test example | 2-1 | 2-2 | 2-3 | 2-4 | 2-5 | 2-6 |
| --- | --- | --- | --- | --- | --- | --- |
| Ethanol | 5.0 | 5.0 | 5.0 | 5.0 | 5.0 | 5.0 |
| Polyoxyethylene oleylether (15 mol) | 0.8 | 0.8 | 0.8 | 0.8 | 0.8 | 0.8 |
| Methylparaben | 0.1 | 0.1 | 0.1 | 0.1 | 0.1 | 0.1 |
| Trimethylglycine | 5.0 | 5.0 | 5.0 | 5.0 | 5.0 | 5.0 |
| Vitamin A palmitate | 0 | $1 \times 10^{-5}$ | $1 \times 10^{-4}$ | 0.001 | 0.5 | 5.0 |
| Purified water | balance | balance | balance | balance | balance | balance |
| Moisturizing effect | Δ | ○ | ◉ | ◉ | ◉ | ◉ |
| Skin roughness improvement effect | Δ | Δ | ○ | ◉ | ◉ | ◉ |

In test examples 2–3 to 2–6 which were compounded trimethylglycine as a quaternary ammonium salt and vitamin A palmitate as a vitamin A derivatives within the optimum compounding range, the skin lotion was excellent in both moisturizing effect and skin roughness improvement effect.

However, in preserving the skin lotion for a long period, when a large amount of vitamin A palmitate over test example 2–6 was compounded to the skin lotion, it sometimes caused an offensive odor. So the compounding amount of vitamin A palmitate is preferably 5.0% by weight or less.

Because the skin lotion of test example 2-2 was compounded with a relative small amount of vitamin A palmitate as compared with the skin lotion of test examples 2–3 to 2–6, the skin roughness improvement effect of the skin lotion became inconspicuous. However the skin lotion was sufficiently worked the expected effect of the present invention.

TABLE 6

| Test example | 2-7 | 2-8 | 2-9 | 2-10 | 2-11 | 2-12 |
|---|---|---|---|---|---|---|
| Ethanol | 5.0 | 5.0 | 5.0 | 5.0 | 5.0 | 5.0 |
| Polyoxyethylene oleylether (15 mol) | 0.8 | 0.8 | 0.8 | 0.8 | 0.8 | 0.8 |
| Methylparaben | 0.1 | 0.1 | 0.1 | 0.1 | 0.1 | 0.1 |
| Trimethylglycine | 0 | 0.01 | 0.1 | 10.0 | 20.0 | 30.0 |
| Vitamin A palmitate | 0.001 | 0.001 | 0.001 | 0.001 | 0.001 | 0.001 |
| Purified water | balance | balance | balance | balance | balance | balance |
| Moisturizing effect | X | Δ | ○ | ⊚ | ⊚ | ⊚ |
| Skin roughness improvement effect | X | Δ | ○ | ⊚ | ⊚ | ⊚ |

As is clearly from Table 6, 0.01% by weight or more of trimethylglycine was observed moisturizing effect and skin roughness improvement effect. However, the remarkable exhibition of its effect was observed in the case where 0.1% by weight of trimethylglycine was compounded. In test example 2-8, compounding of other moisturizing ingredients improved moisturizing effect.

And, in the case where trimethylglycine was compounded more than 30.0% by weight, a slight powdery feeling appeared.

In these test examples, it was proved that the skin lotion which was compounded vitamin A palmitate as a vitamin A derivatives and trimethylglycine as a quaternary ammonium salt (I) within optimum compounding range was an excellent skin lotion which is sufficiently exhibited the expected effect.

It was also proved that the skin lotion which was compounded these within the preferable compounding range was a skin lotion which was sufficiently fitted for practical use in view of the exhibition of the expected effect.

Other vitamin A derivatives except for vitamin A palmitate which can be compounded to the described external preparation for skin of the present invention is in common with vitamin A palmitate in the basic pharmaceutical effects as a vitamin A derivatives. Therefore, in case of compounding these other vitamin A derivatives by the formulation which corresponds to the properties of each vitamin A derivative in place of vitamin A palmitate, an excellent skin lotion can be provided like the above-mentioned test examples.

Next, milky lotion was prepared by the formulation of the following described Table 7, the effectiveness of the external preparation for skin of the present invention was studied by doing the above-described water retention test and skin roughness improvement test.

TABLE 7

| | Example | |
|---|---|---|
| | 2-1 | 2-2 |
| (Oil phase) | | |
| Squalane | 10.0 | 10.0 |
| Petrolatum | 2.0 | 2.0 |
| Cetanol | 1.0 | 1.0 |
| Lanolin alcohol | 2.0 | 2.0 |
| Liquid paraffin | 8.0 | 8.0 |
| Vitamin A acetate | 0.001 | $1 \times 10^{-4}$ |
| Antiseptic agent | 0.2 | 0.2 |

TABLE 7-continued

| | Example | |
|---|---|---|
| | 2-1 | 2-2 |
| Perfume | 0.05 | 0.05 |
| (Water phase) | | |
| Carboxyvinyl polymer | 0.2 | 0.2 |
| Alkyl denatured carboxyvinyl polymer | 0.7 | 0.7 |
| KOH | 0.3 | 0.3 |
| γγ-butyrobetoine | 5.0 | 5.0 |
| Purified water | balance | balance |
| Moisturizing effect | ⊚ | ⊚ |
| Skin roughness improvement effect | ⊚ | ○ |

(Process)

It was preemulsified by adding the heated and dissolved oil phase at 70° C. to the water phase of 70° C., and further uniformly emulsified by a homomixer. After this, it was cooled down to 30° C., and the milky lotion was obtained.

The milky lotion in accordance with the example 2-1 which was compounded γbutyrobetaine as a quaternary ammonium salt (I) and vitamin A acetate as a vitamin E types within the optimum compounding range was particularly excellent in both moisturizing effect and skin roughness improvement effect.

Since the compounding amount of vitamin A acetate was relatively small as compared with example 1, the milky lotion in accordance with the example 2-2 became inconspicuous in skin roughness improvement effect. But, the milky lotion was sufficiently worked the expected effect of the present invention.

And, all the milky lotions of these examples were not accompanied with the powdery feel of use.

In these examples, the milky lotion which was compounded the vitamin A derivatives and the quaternary ammonium salt (I) within the optimum compounding range, can sufficiently exhibit the expected effect. And, the milky lotion which was compounded the vitamin A derivatives and the quaternary ammonium salt within the preferable compounding range, was sufficiently fitted for practical use in view of exhibiting the expected effect.

Quaternary Ammonium Salt and Alkyl Denatured Carboxyvinyl Polymer

Next, the inventors manufactured the composition which is described in Table 8 and Table 9, and the study further proceeded about the mutual relation between the quaternary ammonium salt and alkyl denatured carboxyvinyl polymer.

In case of using combined a quaternary ammonium salt and alkyl denatured carboxyvinyl polymer, if both the components are low concentrations, the composition is in a liquid state. However, if both the components are high concentrations, the composition forms a gel. This gel formative action is the phenomenon which is differentially seen by the combination of the quaternary ammonium salt and alkyl denatured carboxyvinyl polymer. This gel formative action has been done by the following test.

[Gel formative property (viscosity)]

The viscosity of each samples was measured by a roater No. 3 at 30° C. by using a single cylindrical rotating viscometer (VS-A1 type) produced by Seiki Kogyo Kenkyusho (Co.,ltd.). This viscosity was evaluated as the indication of the gel formative property.

(Evaluation)

⊚: Viscosity 1,500 or more (cps/30° C.)
o: Viscosity in the range from 500 to 1,500 (cps/30° C.)
Δ: Viscosity in the range from 100 to 500 (cps/30° C.)
X: Viscosity less than 100 (cps/30° C.)

TABLE 8

| Test example | 3-1 | 3-2 | 3-3 | 3-4 | 3-5 | 3-6 |
|---|---|---|---|---|---|---|
| Ethanol | 20.0 | 20.0 | 20.0 | 200. | 20.0 | 20.0 |
| Polyoxyethylene oleyl ether (15 mol) | 1.0 | 1.0 | 1.0 | 1.0 | 1.0 | 1.0 |
| Methylparaben | 0.1 | 0.1 | 0.1 | 0.1 | 0.1 | 0.1 |
| Trimethylglycine | 7.0 | 7.0 | 7.0 | 7.0 | 7.0 | 7.0 |
| Alkyl denatured carboxyvinyl polymer | 0 | 0.01 | 0.05 | 2.0 | 5.0 | 8.0 |
| Purified water | balance | balance | balance | balance | balance | balance |
| Moisturizing effect | Δ | ⊚ | ⊚ | ⊚ | ⊚ | ⊚ |
| Skin roughness improvement effect | Δ | ⊚ | ⊚ | ⊚ | ⊚ | ⊚ |
| Gel formative property (Viscosity) | X | Δ | o | ⊚ | ⊚ | ⊚ |

Alkyl denatured carboxyvinyl polymer: [CARBOPOL 1342]

(Process)

Polyoxyethylene oleyl ether and methylparaben were dissolved into ethanol (ethanol phase). Aside from this, the dissolution (water phase) was prepared by dissolving alkyl denatured carboxyvinyl polymer and trimethylglycine into ion-exchanged water. And then, the ethanol phase was added to the water phase and the skin lotion was obtained by solubilizing and dissolving it.

In test examples 3-3 to 3-6 which were compounded trimethylglycine as the quaternary ammonium salt and alkyl denatured carboxyvinyl polymer within the optimum compounding range, the skin lotion was excellent in both moisturizing effect and skin roughness improvement effect. However in test example 3-6, since the skin lotion had a tendency to worsen the feel of use because the gel viscosity become too high. The amount of alkyl denatured carboxyvinyl polymer is preferably 5.0% by weight or less.

TABLE 9

| Test example | 3-7 | 3-8 | 3-9 | 3-10 | 3-11 | 3-12 |
|---|---|---|---|---|---|---|
| Ethanol | 20.0 | 20.0 | 20.0 | 20.0 | 20.0 | 20.0 |
| Polyoxyethylene oleyl ether (15 mol) | 1.0 | 1.0 | 1.0 | 1.0 | 1.0 | 1.0 |
| Methylparaben | 0.1 | 0.1 | 0.1 | 0.1 | 0.1 | 0.1 |
| Trimethylglycine | 0 | 0.01 | 0.1 | 5.0 | 20.0 | 30.0 |
| Alkyl denatured carboxyvinyl polymer | 0.1 | 0.1 | 0.1 | 0.1 | 0.1 | 0.1 |
| Purified water | balance | balance | balance | balance | balance | balance |
| Moisturizing effect | X | Δ | o | ⊚ | ⊚ | ⊚ |
| Skin roughness improvement effect | X | o | ⊚ | ⊚ | ⊚ | ⊚ |
| Gel formative property (Viscosity) | X | Δ | Δ | o | ⊚ | ⊚ |

Alkyl denatured carboxyvinyl polymer: PEMULEN TR-2

As is clearly from Table 9, the moisturizing effect by compounding 0.01% by weight or more of trimethylglycine can be observed, but the effect is remarkably exhibited in the case where the compounding amount of trimethylglycine is 0.1% by weight or more. In test example 3–8, moisturizing effect was improved by further compounding the other moisturizing ingredients.

In the case where trimethylglycine is compounded 30.0% by weight or more, the slight powdery feeling was appeared.

From the results of these test examples, it is understood that the skin lotion which was compounded alkyl denatured carboxyvinyl polymer and trimethylglycine as the quaternary ammonium salt (I) within the optimum compounding range was an excellent skin lotion which was sufficiently exhibited the expected effect.

And, it was proved that the skin lotion which was compounded the alkyl denatured carboxyvinyl polymer and trimethylglycine (quaternary ammonium) within the preferable compounding range was sufficiently fitted for practical use in view of exhibiting the expected effect.

Next, the milky lotion by the formulation of Table 10 was prepared, and the effectiveness of the external preparation for skin of the present invention was studied by doing the above-mentioned water retention test and skin roughness improvement test.

TABLE 10

| | Example | Comparative example | |
|---|---|---|---|
| | 3-1 | 3-1 | 3-2 |
| Alkyl denatured carboxyvinyl polymer | 0.1 | 0.1 | 0.1 |
| γ-Butyrobetaine | 5.0 | — | — |
| 1,3-butylene glycol | — | — | 5.0 |
| Potassium hydroxide | — | 0.04 | 0.04 |
| Purified water | balance | balance | balance |
| Moisturizing effect | ⊚ | Δ | o |
| Skin roughness improvement effect | ⊚ | X | Δ |
| Gel formative property (Viscosity) | o | o | o |

Alkyl denatured carboxyvinyl polymer: [CARBOPOL 1342]

(Process)

Example 3-1 was formed the proper viscosity gel without using the base (potassium hydroxide) as a neutralizer, and the moisturizing effect was observed to be stronger than comparative example 3-2 which was compounded a humectant.

In the following, the compounding examples of the present invention will be explained more concretely. The external preparation for skin in accordance with the following compounding examples all show an excellent moisturizing effect and skin roughness improvement effect.

Compounding example 1-1
Cream

|  | % by weight |
|---|---|
| Oil phase | |
| Squalane | 10.0 |
| Stearic acid | 2.0 |
| Petrolatum | 2.0 |
| Cetanol | 1.0 |
| Lanolin alcohol | 2.0 |
| Liquid paraffin | 8.0 |
| dl-α-tocopherol | 0.1 |
| Antiseptic agent | 0.2 |
| Perfume | 0.05 |
| Water phase | |
| Carboxyvinyl polymer | 0.2 |
| Sodium chondroitin sulfate | 1.0 |
| Trimethylglycine | 3.0 |
| KOH | 0.06 |
| Purified water | balance |

(Process)

After dissolving sodium chondroitin sulfate and trimethylglycine into one part of purified water, dissolving carboxyvinyl polymer and KOH into the other part of purified water. And mixing them and the water phase part is prepared. After adding the above-described oil phase part which was uniformly dissolved, to the water phase part, treating it by a homomixer. Stirring and cooling it down, the expected cream was obtained.

Compounding example 1-2
After-shave lotion

|  | % by weight |
|---|---|
| Alcohol phase | |
| Polyoxyethylene alkyl ether | 0.8 |
| Menthol | 0.01 |
| Antiseptic agent | 0.1 |
| Perfume | 0.1 |
| Ethyl alcohol | 20.0 |
| Vitamin E acetate | 0.02 |
| Water phase | |
| Sodium glycyrrhizinate | 0.01 |
| Trimethylglycine | 1.0 |
| Purified water | balance |

(Process)

After dissolving the water phase components into purified water, adding to the alcohol phase components which was dissolved into ethyl alcohol, while stirring, the expected after-shave lotion was obtained.

Compounding example 1-3
Mask

|  | % by weight |
|---|---|
| Dipropylene glycol phase | |
| Dipropylene glycol | 3.0 |
| Methyl cellulose | 0.05 |
| Antiseptic agent | 0.2 |
| d-δ-tocopherol | 0.05 |
| Water phase | |
| Carboxyvinyl polymer | 0.5 |
| Trimethylglycine | 2.0 |
| KOH | 0.15 |
| Purified water | balance |

(Process)

After heating and dissolving an antiseptic agent to dipropylene glycol, preparing the dipropylene glycol phase by adding methyl cellulose. And, adding carboxyvinyl polymer which was dissolved in one part of purified water and trimethylglycine and KOH which was dissolved in the other part of purified water to this, the expected mask was obtained.

Compounding example 1-4
Skin lotion

|  | % by weight |
|---|---|
| Alcohol phase | |
| POE oleyl alcohol ether | 1.0 |
| Olive oil | 0.2 |
| Antiseptic agent | 0.2 |
| Ethyl alcohol | 7.0 |
| Vitamin E acetate | 0.1 |
| Water phase | |
| Sorbitol | 8.0 |
| 1,3 Butylene glycol | 5.0 |
| Polyethylene glycol 1500 | 7.0 |
| Hyaluronic acid | 0.1 |
| Trimethylglycine | 2.0 |
| Purified water | balance |

(Process)

The water phase was obtained by dissolving the above-stated water phase components to purified water. Next, POE oleyl ether, olive oil, and antiseptic agent were dissolved into ethanol successively. After heating and dissolving oil phrase into water phase and the expected skin lotion was obtained.

Compounding example 2-1
Cream

|  | % by weight |
|---|---|
| Oil phase | |
| Squalane | 10.0 |
| Stearic acid | 2.0 |
| Petrolatum | 2.0 |
| Cethanol | 1.0 |
| Lanolin alcohol | 2.0 |
| Liquid paraffin | 8.0 |
| Vitamin A palmitate | 0.01 |
| Antiseptic agent | 0.2 |
| Perfume | 0.05 |
| Water phase | |
| Carboxyvinyl polymer | 0.2 |
| Sodium chondroitin sulfate | 1.0 |

Compounding example 2-1
Cream

|  | % by weight |
|---|---|
| Trimethylglycine | 5.0 |
| KOH | 0.06 |
| Purified water | balance |

(Process)

After dissolving sodium chondroitin sulfate and trimethylglycine into a part of purified water, and dissolving carboxyvinyl polymer and KOH into other part of purified water. Mixing them and the water phase part was prepared. After adding the above-described oil phase part which was uniformly dissolved, to the water phase part, treating it by a homomixer. Stirring it and cooling it down, the expected cream was obtained.

Compounding example 2-2
After-shave lotion

|  | % by weight |
|---|---|
| Alcohol phase | |
| Polyoxyethylene alkyl ether | 0.8 |
| Menthol | 0.01 |
| Antiseptic agent | 0.1 |
| Perfume | 0.1 |
| Ethyl alcohol | 20.0 |
| Vitamin A acetate | 0.001 |
| Water phase | |
| Sodium glycyrrhizinate | 0.01 |
| Trimethylglycine | 2.0 |
| Purified water | balance |

(Process)

After dissolving the water phase components into purified water, and adding the alcohol phase components which were dissolved into ethyl alcohol, to the water phase while stirring, the expected after-shave lotion was obtained.

Compounding example 2-3
Mask

|  | % by weight |
|---|---|
| Dipropylene glycol phase | |
| Dipropylene glycol | 3.0 |
| Methyl cellulose | 0.05 |
| Antiseptic agent | 0.2 |
| Vitamin A palmitate | 0.01 |
| Water phase | |
| Carboxyvinyl polymer | 0.5 |
| Trimethylglycine | 5.0 |
| KOH | 0.15 |
| Purified water | balance |

(Process)

After heating and dissolving an antiseptic agent to dipropylene glycol, preparing dipropylene glycol phase by adding methyl cellulose. And, adding carboxyvinyl polymer which was dissolved into a part of purified water and trimethylglycine and KOH which was dissolved into other part of purified water to this, the expected mask was obtained.

Compounding example 2-4
Skin lotion

|  | % by weight |
|---|---|
| Alcohol phase | |
| POE oleyl alcohol ether | 1.0 |
| Olive oil | 0.2 |
| Antiseptic agent | 0.2 |
| Ethyl alcohol | 7.0 |
| Vitamin A palmitate | 0.01 |
| Water phase | |
| Sorbitol | 8.0 |
| 1,3 Butylene glycol | 5.0 |
| Polyethylene glycol 1500 | 7.0 |
| Hyaluronic acid | 0.1 |
| γ-Butyrobetaine | 2.0 |
| Purified water | balance |

(Process)

The water phase was obtained by dissolving the above-stated water phase component to purified water. Next, POE oleyl ether, olive oil, and antiseptic agent were dissolved into ethanol successively. After heating and dissolving alcohol phase into water phase, the expected skin lotion was obtained.

Compounding example 3-1

|  | % by weight |
|---|---|
| A. Oil phase | |
| Squalane | 10.0 |
| Isopropyl palmitate | 5.0 |
| POE (25) cetyl ether | 0.5 |
| Petrolatum | 3.0 |
| Dimethyl polysiloxane | 2.0 |
| Hexyldecanol | 3.0 |
| α-tocopherol | 0.3 |
| B. Water phase | |
| Polyethylene glycol | 8.0 |
| Methyl parahydroxybenzoate | 0.1 |
| Sodium metaphosphate | 0.1 |
| Alkyl denatured carboxyvinyl polymer ([CARBOPOL 1342]) | 0.5 |
| Trimethylglycine | 20.0 |
| Ion-exchanged water | balance |

(Process)

By Heating and dissolving phase A (oil phase) components to 70° C., heating and dissolving phase B (water phase) components to 70° C. in the same way as phase A. Emulsifying by adding phase B components to phase A components while sufficiently treating by a homogenizer, and cooling it down by a heat exchanger, and the emulsion composition was obtained.

(Evaluation)

The obtained emulsion composition had good gel formative property (viscosity), and was excellent in moisturizing property and skin roughness improvement effect.

Compounding example 3-2

| | % by weight |
|---|---|
| A. Oil phase | |
| Liquid paraffin | 10.0 |
| Jojoba oil | 4.0 |
| Dimethyl polysiloxane (10 cs) | 3.0 |
| POE (15) sorbitan monostearate | 1.0 |
| Glyceryl monostearate | 0.5 |
| Vitamin A oil | 3.0 |
| B. Water phase | |
| Arbutin | 2.0 |
| Magnesium ascorbyl phosphate | 1.0 |
| Placenta extract | 0.5 |
| Trisodium EDTA | 0.15 |
| Alkyl denatured carboxyvinyl polymer ([CARBOPOL 1342]) | 0.15 |
| Methylparabenzoate | 0.1 |
| Phenoxyethanol | 0.2 |
| γ-Butyrobetaine | 0.1 |
| Ion-exchanged water | balance |

(Process)

By heating and dissolving phase A (oil phase) components to 70° C., heating and dissolving phase B (water phase) components to 70° C. in the same way as phase A. Emulsifying by adding phase B components to phase A components with sufficiently treated by a homogenizer and cooling it down by a heat exchanger, the emulsion composition was obtained.

(Evaluation)

The obtained emulsion composition had a good gel formative property (viscosity), and was excellent in moisturizing property and skin roughness improvement effect.

Compounding example 3-3

| | % by weight |
|---|---|
| A. Oil phase | |
| Stearic acid | 2.0 |
| Cetyl alcohol | 1.5 |
| Petrolatum | 4.0 |
| Squalane | 5.0 |
| Glycerol tri(2-ethylhexanoate) | 2.0 |
| Sorbitan monooleate | 2.0 |
| 2-ethylhexyl 4-methoxycinnamate | 2.0 |
| dl-tocopheryl acetate | 0.5 |
| Ethyl parahydroxybenzoate | 0.1 |
| B. Water phase | |
| Dipropylene glycol | 5.0 |
| Polyethylene glycol (1500) | 0.15 |
| Trisodium EDTA | 5.0 |
| Alkyl denatured carboxyvinyl polymer ([CARBOPOL 1342]) | 5.0 |
| Carboxy methyl cellulose | 0.8 |
| Trimethylglycine | 10.0 |
| Potassium hydroxide | 1.0 |
| Ion-exchanged water | balance |

(Process)

Using a part of ion-exchanged water of phase B, and the gel was formed by dissolving [CARBOPOL 1342] and trimethylglycine into this. By heating and dissolving Phase A (oil phase) components to 70° C., heating and dissolving Phase B (water phase; except for [CARBOPOL 1342] and trimethylglycine) components to 70° C. in the same way as phase A components. Emulsifying by adding phase B components to phase A components while sufficiently treating by a homogenizer and cooling it down by a heat exchanger, the emulsion composition was obtained.

(Evaluation)

The obtained emulsion composition had a good gel formative property (viscosity), and was excellent in moisturizing property and skin roughness improvement effect.

Compounding example 3-4

| | % by weight |
|---|---|
| Sorbitol | 4.0 |
| Dipropylene glycol | 6.0 |
| Polyethylene glycol | 5.0 |
| Ethanol | 10.0 |
| POE (20) oleyl alcohol ether | 0.5 |
| Alkyl denatured carboxyvinyl polymer ([CARBOPOL 1342]) | 0.15 |
| γ-Butyrobetaine | 0.8 |
| Ion-exchanged water | balance |

(Process)

Using a part of ion-exchanged water, and the gel was obtained by dissolving [CARBOPOL 1342] and γ-Butyrobetaine into this. By adding sorbitol, dipropylene glycol, and polyethylene glycol (1500) after heating to 70° C. to the balance of ion-exchange water. And then, by adding the above-mentioned gel to this, an uniform water solution was obtained. After preparing an alcohol solution by adding POE (20) oleyl alcohol to ethanol, the solubilized composition was obtained by adding this alcohol solution to the above-mentioned uniform water solution.

(Evaluation)

The obtained solubilizing composition had a good gel formative property (viscosity) and excellent moisturizing property, and also had a skin roughness improvement effect.

We claim:

1. An external preparation for skin consisting essentially of:

a quaternary ammonium salt having the formula (I) of:

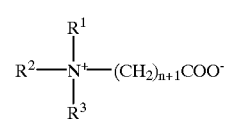

(I)

wherein $R^1$, $R^2$, and $R^3$ are alkyl groups having a carbon number from 1 to 6, wherein the total numbers of carbon in $R^1$, $R^2$, $R^3$ and n is 8 or less, and wherein the carbon number of $R^1$, $R^2$, $R^3$ is the same or different; and an enhancer for the quaternary ammonium salt, wherein said enhancer improves moisturizing effect of the quaternary ammonium salt, wherein said enhancer is selected from the group consisting of at least one of a vitamin E derivative, a vitamin A derivative, and an acrylate alkyl methacrylate copolymer.

2. The external preparation according to claim 1, wherein the amount of said quaternary ammonium salt is in the range from 0.1% by weight to 30% by weight with respect to the whole amount of the external preparation.

3. The external preparation according to claim 1, wherein the amount of said quaternary ammonium salt is in the range from 0.1% by weight to 20% by weight with respect to the whole amount of the external preparation.

4. The external preparation according to claim 1, wherein said vitamin E derivative is at least one selected from the group consisting of tocopherol, vitamin E acetate, vitamin E nicotinate, and α-tocopherol-2, L-ascorbic acid phosphate diester.

5. The external preparation according to claim 4, wherein the amount of said vitamin E derivative is in the range from 0.0001% by weight to 2.0% by weight with respect to the whole amount of the external preparation.

6. The external preparation according to claim 4, wherein the amount of said vitamin E derivative is in the range from 0.001% by weight to 0.5% by weight with respect to the whole amount of the external preparation.

7. The external preparation according to claim 1, wherein said vitamin A derivative is vitamin A ester.

8. The external preparation according to claim 7, wherein the amount of said vitamin A derivative is in the range from $1\times10^{-5}$% by weight to 5.0% by weight with respect to the whole amount of the external preparation.

9. The external preparation according to claim 7, wherein the amount of said vitamin A derivative is in the range from $1\times10^{-4}$% by weight to 0.5% by weight with respect to the whole amount of the external preparation.

10. The external preparation according to claim 1, wherein the amount of said acrylate alkyl methacrylate copolymer is in the range from 0.01% by weight to 5.0% by weight with respect to the whole amount of the external preparation.

11. The external preparation according to claim 1, wherein the amount of said acrylate alkyl methacrylate copolymer is in the range from 0.05% by weight to 2.0% by weight with respect to the whole amount of the external preparation.

12. The external preparation according to claim 1, wherein said quaternary ammonium salt is trimethyl glycine.

* * * * *